US005858335A

United States Patent [19]
Lucas et al.

[11] Patent Number: 5,858,335
[45] Date of Patent: Jan. 12, 1999

[54] METHOD OF REDUCING BODY ODOR USING PERFUME-FREE TWO PHASE COMPOSITIONS

[75] Inventors: Juliet Marie Lucas, Cincinnati; Toan Trinh, Maineville; Robin Yager Buckner, Cincinnati; Theresa Marie Kajs, Loveland, all of Ohio

[73] Assignee: The Procter & Gamble Company, Cincinnati, Ohio

[21] Appl. No.: 871,860

[22] Filed: Jun. 9, 1997

[51] Int. Cl.$^6$ .................... A61K 7/32; A61K 33/24; A61K 25/00; A61K 33/10
[52] U.S. Cl. .................. 424/65; 422/5; 424/67; 424/69; 424/76.1; 424/76.2; 424/76.21; 424/76.4; 424/76.8; 424/78.03; 424/405; 424/642; 424/715; 424/717
[58] Field of Search ................ 424/65, 67, 69, 424/76.1, 76.2, 76.21, 76.4, 76.8, 78.03, 642, 715, 717, 405; 422/5

[56] References Cited

U.S. PATENT DOCUMENTS

| | | | |
|---|---|---|---|
| 3,574,821 | 4/1971 | Pfirrmann et al. | 424/45 |
| 4,278,658 | 7/1981 | Hooper et al. | 424/65 |
| 4,382,079 | 5/1983 | Marschner | 424/65 |
| 4,659,696 | 4/1987 | Hirai et al. | 514/15 |
| 4,788,060 | 11/1988 | Endicott et al. | 424/443 |
| 4,822,602 | 4/1989 | Sabatelli | 424/65 |
| 4,904,524 | 2/1990 | Yoh | 428/311.3 |
| 5,429,628 | 7/1995 | Trinh et al. | 604/359 |
| 5,486,355 | 1/1996 | Berschied, Jr. | 424/65 |
| 5,512,199 | 4/1996 | Khan et al. | 252/106 |
| 5,514,367 | 5/1996 | Lentini et al. | 424/59 |
| 5,518,727 | 5/1996 | Lajoie et al. | 424/400 |
| 5,552,378 | 9/1996 | Trinh et al. | 512/3 |
| 5,578,563 | 11/1996 | Trinh et al. | 510/513 |
| 5,580,851 | 12/1996 | Trinh et al. | 512/4 |
| 5,593,670 | 1/1997 | Trinh et al. | 424/76.1 |
| 5,635,165 | 6/1997 | Panitch | 424/65 |

FOREIGN PATENT DOCUMENTS

| | | |
|---|---|---|
| 0 613 675 A1 | 9/1994 | European Pat. Off. . |
| 0 701 812 A1 | 3/1996 | European Pat. Off. . |
| 2201880 | 5/1974 | France . |
| 87637 | 11/1972 | Germany . |
| 2731520 | 1/1979 | Germany . |
| 208482 B | 8/1992 | Hungary . |
| 53-41440 | 4/1978 | Japan . |
| 58-124452 | 7/1983 | Japan . |
| 63-128973 | 6/1986 | Japan . |
| 63-164953 | 7/1988 | Japan . |
| 3-170415 | 7/1991 | Japan . |
| 3-284616 | 12/1991 | Japan . |
| 5-269185 | 10/1993 | Japan . |
| WO 95/17175 | 6/1995 | WIPO . |

OTHER PUBLICATIONS

Hashimoto, H., "Studies on the Industrial Production and Application of Cyclodextrins", Starch Science, vol. 36, No. 1 (1989), pp. 35–42.

U.S. application No. 08/736,469, Trinh et al., filed Oct. 24, 1996.
U.S. application No. 08/736,093, Trinh et al., filed Oct. 24, 1996.
U.S. application No. 08/889,607, Trinh et al., filed Jul. 8, 1997.
U.S. application No. 08/736,471, Lucas et al., filed Oct. 24, 1996.
U.S. application No. 08/736,470, Lucas et al., filed Oct. 24, 1996.
U.S. application No. 08/738,964, Dodd et al., filed Oct. 24, 1996.
U.S. application No. 08/736,838, Peterson et al., filed Oct. 28, 1996.
U.S. application No. 08/739,091, Peterson et al., filed Oct. 28, 1996.
U.S. application No. 08/871,166, Lucas et al., filed Jun. 9, 1997.
U.S. application No. 08/871,854, Lucas et al., filed Jun. 9, 1997.
U.S. application No. 08/871,791, Dodd et al., filed Jun. 9, 1997.
U.S. application No. 08/871,855, Trinh et al., filed Jun. 9, 1997.
U.S. application No. 08/871,853, Lucas et al., filed Jun. 9, 1997.
U.S. application No. 08/871,857, Lucas et al., filed Jun. 9, 1997.
U.S. application No. 08/871,790, Peterson et al., filed Jun. 9, 1997.
U.S. application No. 08/871,856, Peterson et al., filed Jun. 09, 1997.
U.S. application No. 08/871,858, Lucas et al., filed Jun. 9, 1997.
U.S. application No. 08/871,577, Lucas et al., filed Jun. 9, 1997.
U.S. application No. 08/871,861, Peterson et al., filed Jun. 9, 1997.

(List continued on next page.)

*Primary Examiner*—Shelley A. Dodson
*Attorney, Agent, or Firm*—Kirsten K. Stone; Mary Catherine Hentz; Douglas C. Mohl

[57] ABSTRACT

The present invention relates to methods of reducing body and/or vaginal odor comprising the application to skin of perfume-free, odor absorbing compositions comprising from about 0.1% to about 5%, by weight of the composition, of solubilized, water-soluble, uncomplexed cyclodextrin; from about 0.1% to about 36%, by weight of the composition, of an oil phase selected from the group consisting of emollients, moisturizers, skin protectants, and mixtures thereof; one or more surfactants each having a hydrophilic/lipophilic balance of about 8–18 and wherein each surfactant, when combined with an aqueous cyclodextrin solution, provides no less than about 25% a level of odor capture as an aqueous cyclodextrin solution; and an aqueous carrier wherein the odor absorbing composition is safe for use on skin. The odor absorbing compositions may also, preferably, contain an effective amount of hydrophobic antimicrobials.

20 Claims, No Drawings

OTHER PUBLICATIONS

U.S. application No. 08/871,092, Peterson et al., filed Jun. 9, 1997.
U.S. application No. 08/289,732, Trinh et al., filed Aug. 12, 1994.
U.S. application No. 08/289,733, Trinh et al., filed Aug. 12, 1994.
U.S. application No. 08/289,734, Cappel et al., filed Aug. 12, 1994.
U.S. application No. 08/289,735, Cappel et al., filed Aug. 12, 1994.
U.S. application No. 08/289,969, Pilosof et al., filed Aug. 12, 1994.
U.S. application No. 08/871,576, Woo et al., filed Jun. 9, 1997.
U.S. application No. 08/871,119, Woo et al., filed Jun. 9, 1997.
U.S. application No. 08/871,042, Woo et al., filed Jun. 9, 1997.

METHOD OF REDUCING BODY ODOR USING PERFUME-FREE TWO PHASE COMPOSITIONS

BACKGROUND OF THE INVENTION

Body odor is most commonly caused by fatty acids on skin and by malodors from microbial sources. The human skin is naturally populated with numerous micro-organisms which are nourished by various skin secreted substances (eccrine and apocrine sweat, and sebum), skin cell debris, breakdown products of the skin and the organisms themselves. These unpleasant body odors are mainly organic molecules which have different structures and functional groups, such as amines, acids, alcohols, aldehydes, ketones, phenolics, polycyclics, indoles, aromatics, polyaromatics, etc. They can also be made up of sulfur-containing functional groups, such as, thiol, mercaptan, sulfide and/or disulfide groups.

Numerous attempts have been made to control or absorb body odors. Attempts have been made to deprive the microbials responsible for body odor of the moist/humid environment they need to proliferate and grow. Such efforts include the use of powders and/or antiperspirants. Body powders often are undesirable as they may be difficult to apply and may rub or fall off onto clothing. Antiperspirants are not always preferred in a body odor control product since, when used over the entire body, they may interfere with the body's thermal regulatory process by inhibiting perspiration through the action of astringent salts. Additionally, such salts may be irritating to a large number of users, particularly when applying them to sensitive areas such as the pelvic region.

Other deodorant compositions aimed at combating/controlling odor associated with skin secretions, which have been described in the chemical and cosmetic literature, include emulsion sticks or suspensoid sticks, aerosols, roll-ons, pads, pump sprays, and even soap bars. These known deodorants attempt to control odor through a variety of means. For instance, U.S. Pat. No. 5,525,331, to Betts, issued Jun. 11, 1996, discloses compositions which inhibit the growth of micro-organisms in the body-secretions. Deodorants may also include antibacterial compounds which help destroy/control the amount of bacteria present on skin, thereby minimizing odor produced via bacterial metabolism of skin secretions.

Zeolites are known odor absorbers. However, these solid odor absorbers, in addition to known activated charcoal odor absorbers, lose functionality when wet. Therefore, when wetted by body fluids or when carried in an aqueous solution, these odor absorbers are not preferred as they lose their desired odor absorbent characteristics. Furthermore, zeolites can cause "harsh" feel if too much is deposited onto the skin.

In addition to the aforementioned attempts at controlling and/or absorbing body odor, numerous attempts have been made to mask body odors with other odors or perfumes. However, perfumes are often inadequate at fully concealing body odors and may be irritating to the user when used alone for control odor.

Thus, there remains a need for safe and effective methods of reducing body and/or vaginal odor using an odor absorbing composition which is essentially free of perfumes and astringent antiperspirants and which is capable of absorbing a broad spectrum of body odors that are not fully suppressed by the aforementioned means. It has been discovered that such enhanced body odor control can be safely provided to the entire body by application of a composition, which is left on the skin, which incorporates odor absorbing, uncomplexed cyclodextrins into a two phase solution. It has also been discovered that a particular advantage of the present invention is the ability to provide convenient, non-irritating odor protection and optionally skin aid benefits when applied to occluded skin areas such as the pelvic region, the external vagina, the panty-line, the bra-line, and skin-folds, which may be very sensitive.

These and other objects of the present invention will become readily apparent from the detailed description which follows. All percentages, ratios, and parts herein, in the Specification, Examples, and Claims are by weight unless otherwise stated. The term "g", as used herein, means gram. The term "ml", as used herein, means milliliter. The term "wt", as used herein, means weight.

SUMMARY OF THE INVENTION

The present invention relates to methods of reducing body and/or vaginal odor comprising the application to skin of perfume-free, odor absorbing compositions comprising from about 0.1% to about 5%, by weight of the composition, of solubilized, water-soluble, uncomplexed cyclodextrin; from about 0.1% to about 36%, by weight of the composition, of an oil phase selected from the group consisting of emollients, moisturizers, skin protectants, and mixtures thereof; one or more surfactants each having a hydrophilic/lipophilic balance of about 8–18 and wherein each surfactant, when combined with an aqueous cyclodextrin solution, provides no less than about 25% a level of odor capture as an aqueous cyclodextrin solution; and an aqueous carrier wherein the odor absorbing composition is safe for use on skin. The odor absorbing compositions may also, preferably, contain an effective amount of hydrophobic antimicrobials.

DETAILED DESCRIPTION OF THE INVENTION

The present invention relates to a method of reducing body and or vaginal odor comprising the application of a perfume-free odor-absorbing composition. The composition can be applied directly as a spray, poured from a bottle and applied by hand, or applied via a wipe which is wet. The present invention also relates also relates to use of an article of manufacture comprising the odor-absorbing composition deposited on a flexible dispensing means.

The term "body fluids", as used herein, includes eccrine sweat, apocrine sweat, sebum, build up of sensible moisture from transepidermal water loss, vaginal discharge, urine, and mixtures thereof. The term "body odor" as used herein means odors which are generated as a result of the natural functioning of a human or mammalian body. Such odors include, but are not limited to odors produced by microorganisms of the skin (i.e. bacterial decomposition of skin secretions), urine, or vaginal discharge, and mixtures thereof. The term "skin" means human or mammalian skin. The term "entire body" means the entire external surface of human or mammalian skin. The term "vaginal odor" relates specifically to those body odors which emanate from the pelvic region of a woman, particularly the vagina and the panty line. The phrase "safe for use on skin", as used herein, means that the composition provides the desired benefit without undue adverse side effects.

A detailed description of the methods, and of the essential and optional components of the odor absorbing compositions useful in the present invention is given below.

CYCLODEXTRIN: As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The term "uncomplexed cyclodextrin" as used herein means that the cavities within the cyclodextrin in the solution of the present invention should remain essentially unfilled while in solution, in order to allow the cyclodextrin to absorb various odor molecules when the solution is applied to a surface. The term "water-soluble, uncomplexed cyclodextrin" as used herein means uncomplexed cyclodextrin having a minimum solubility limit of 1% (1 gram in 100 grams of water).

Preferred, the cyclodextrins used in the present invention are highly water-soluble such as, alpha-cyclodextrin and/or derivatives thereof, gamma-cyclodextrin and/or derivatives thereof, derivatised beta-cyclodextrins, and/or mixtures thereof. The derivatives of cyclodextrin consist mainly of molecules wherein some of the OH groups are converted to OR groups. Highly water-soluble cyclodextrins are those having water solubility of at least about 10 g in 100 ml of water at room temperature, preferably at least about 20 g in 100 ml of water, more preferably at least about 25 g in 100 ml of water at room temperature. The preferred highly water-soluble cyclodextrins are hydroxypropyl beta-cyclodextrin and methylated beta-cyclodextrin. More preferred are beta cyclodextrin, hydroxypropyl alpha-cyclodextrin, hydroxypropyl beta-cyclodextrin, methylated-alpha-cyclodextrin or methylated-beta-cyclodextrin. Non-derivatised beta-cyclodextrin can be present at a level up to its solubility limit of about 1.85% at room temperature. When beta-cyclodextrin is applied to a wipe substrate, levels higher than its solubility limit can be used.

It is also preferable to use a mixture of cyclodextrins. Such mixtures absorb body odors more broadly by complexing with a wider range of odoriferous molecules having a wider range of molecular sizes. Preferred are mixtures of beta-cyclodextrin and/or its derivatives with alpha-cyclodextrin and/or its derivatives, and mixtures thereof. The levels of cyclodextrin are from about 0.1% to about 5%, preferably from about 0.2% to about 4%, more preferably from about 0.3% to about 3%, most preferably from about 0.4% to about 2%, by weight of the composition.

Concentrated compositions can also be used. When a concentrated product is used, i.e., when the level of cyclodextrin used is from about 3% to about 10%, it is preferable to dilute the composition before applying to the skin in order to avoid tacky skin feel and/or an undesirable amount of residue. Preferably the cyclodextrin is diluted with about 50% to about 2000%, more preferably with about 60% to about 1000%, most preferably with about 75% to about 500%, by weight of the composition, of water.

The complexation between cyclodextrin and odorous molecules occurs rapidly in the presence of water when the solubilized cyclodextrins are first applied to the skin. Additionally, cyclodextrins which dry on the skin surfaces will once again achieve enhanced absorption capabilities when rewetted with body fluids. This is convenient for the user because the cyclodextrins, while on dry skin, will not readily fill their cavities with other environmental odors which would otherwise render them less efficient for absorbing body odors. More particularly, upon solubilization of the cyclodextrins by the body fluids, the isolated cavities become available to form inclusion complexes with the body odor molecules. Thus, ultimately, the availability of solubilized uncomplexed cyclodextrin is essential for an effective and efficient odor control performance. A more complete description of the cyclodextrins and cyclodextrin derivatives useful in the present invention can be found in U.S. Pat. No. 5,534,165, Pilosof et al., issued Jul. 9, 1996, which is incorporated herein by reference in its entirety.

OIL PHASE: The present invention also includes an oil phase. The oil phase is chosen from the following ingredients: skin protectants, emollients, and/or moisturizers. Saturated or hydrogenated oils are preferred. These ingredients enhance the skin feel characteristics and/or skin care benefits of the present invention. Additionally, the oil phase provides a medium in which hydrophobic antibacterials, if present, may be dissolved.

Skin protectant ingredients can prevent or reduce chafing, skin irritation and/or skin friction that may occur between skin-to-skin contact sites. Preferred skin protectants useful in the present invention include, but are not limited to: vitamin A, cod liver oil, cocoa butter, shark liver oil, dimethicone, petrolatum, white petrolatum, mineral oil, jojoba oil, and lanolin. More preferred are dimethicone, petrolatum, white petrolatum, mineral oil, jojoba oil, and lanolin. Most preferred are the dimethicones.

Moisturizers which aid in adding moisture to the skin may be included in the oil carrier of the present invention. Preferred moisturizers include, but are not limited to vegetable oils and mineral oil. More preferred are hydrogenated or saturated vegetable or mineral oils. Other moisturizers can be chosen from the oily moisturizers in *Cosmetic Bench Ref*, 1994, pages 46–48, incorporated herein by reference.

Emollients for softening and soothing of skin are also useful in the present invention. Emollients useful herein include tocopherol or tocopherol acetate, triglycerides, vegetable oils, or mineral oil. Other emollients can be chosen from the oily emollients in *Cosmetic Bench Ref*, 1994, pages 27–31, incorporated herein by reference.

The oil phase or carrier is present at an "effective level", a level which provides the desired skin benefits of the particular ingredients. Typically, the oil phase is present at a level of from about 0.1% to about 26%, preferably from about 0.2% to about 6%, by weight of the composition.

SURFACTANT: A surfactant must be used in the present invention. Surfactants are known in the art of forming oil-in-water emulsions. Preferably, a combination of surfactants are used for improved stability.

Surfactants suitable for use herein are surfactants which do not have a high level of interaction with the cyclodextrin, thus optimizing the odor absorbing capability of cyclodextrin. Extensive interaction is not desirable as it may diminish the ability of the cyclodextrin to complex with odor causing compounds and the ability of the surfactant to blend the oil and water phases.

The surfactants optimize both the odor absorbing characteristic of cyclodextrin and the blending ability of the surfactant. Such surfactants, when added to an aqueous cyclodextrin solution, provide a surfactant/cyclodextrin solution which demonstrate odor absorption similar to the same cyclodextrin solution without the surfactant. Not desirable are surfactants which, when added to an aqueous cyclodextrin solution, provide a surfactant/cyclodextrin solution which demonstrate odor absorption similar to pure water.

The surfactants can be identified using the procedure which follows. First, within an equilibrium chamber, a paper membrane is sealed to a test cell and wetted with a test sample mixture; or, for purposes of establishing a water control and a cyclodextrin control, the membrane is wetted with water or aqueous cyclodextrin. Test sample mixtures comprise mixtures of a solution of aqueous cyclodextrin and a surfactant or a combination of surfactants. Second, an odor causing challenge compound is injected into the equilibrium chamber and allowed to equilibrate through the paper membrane. The odor causing challenge compounds selected should be those which uncomplexed cyclodextrin is capable of absorbing such as isovaleric acid. Third, after a finite time air in the equilibrium chamber enveloping the test cell is pulled through a Drager tube, which results in a color change within the Drager tube. (Drager tubes are commercially available from Lab Safety, Danesville, Wis.). The distance of color movement up the Drager tube corresponds to the remaining (or uncomplexed) concentration of odorous material within the Drager tube. Replicates of this entire procedure are performed and averages are taken. Any similar procedure such as Gas Chromatograph Head Space Analysis may also be used.

The results from each test sample mixture are then compared to the results of the water control and the cyclodextrin control. As used herein, the phrase "odor capture" refers to the amount of cyclodextrin which complexes with the challenge compound. Thus, a high level of odor capture results in a low level of remaining challenge compound. The surfactant should provide a surfactant/cyclodextrin solution which demonstrates more odor capture than the water control. Preferred surfactants provide a surfactant/cyclodextrin solution which demonstrates no less than about 25%, more preferred no less than about 50%, and even more preferred no less than about 75%, of the level of odor capture as the cyclodextrin control. Most preferred surfactants provide the same level of odor capture as the cyclodextrin control.

Additionally, it is preferable for formation of oil-in-water emulsions that the selected surfactant have a hydrophilic/lipophilic balance ("HLB") of about 8–18. The term HLB is known in the art, for example in U.S. Pat. No. 2,677,700 to Jackson et al., issued May 4, 1954, and incorporated herein by reference. Because of the uniqueness of many of the surfactants mentioned below, they will demonstrate lipophilic behavior different from hydrocarbon lipophiles. Consequently, the HLB values may not correlate exactly with the HLB values for ethylene oxide/hydrocarbon surfactants. Overall, the preferred surfactants for use herein include block copolymers of ethylene oxide and/or propylene oxide and polyalkyleneoxide polysiloxanes. Most preferred are mixtures of at least one of each of block copolymers of ethylene oxide and/or propylene oxide and polyalkyleneoxide polysiloxanes.

Block polyoxyethylene-polyoxypropylene polymeric compounds which are compatible with most cyclodextrins include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as $C_{12-18}$ aliphatic alcohols, are not generally compatible with the cyclodextrin. Block polymer surfactant compounds designated Pluronic® and Tetronic® are commercially available from the BASF-Wyandotte Corp.

Typical block copolymers of ethylene oxide and/or propylene surfactants include: Pluronic® surfactants: $H(EO)_n(PO)_m(EO)_nH$; Reverse Pluronic® surfactants: $H(PO)_n(EO)_m(PO)_nH$; Tetronic® surfactants:

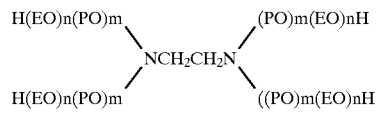

and/or
Reverse Tetronic ® surfactants:

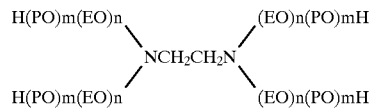

wherein EO is an ethylene oxide group, PO is a propylene oxide group, and n and m are numbers that indicate the average number of the groups in the surfactants. The average molecular weight of the polyoxypropylene polymers in the mixture is between about 900 to about 25,000 and the oxyethylene groups constitute between about 10 to about 90 weight percent of the oxyethylene/oxypropylene mixture. Non-limiting examples of surfactants useful herein having an HLB of about 8 to 18 include: Pluronic® surfactants L10, L43, L44, L63, L64, L65, P75, P84, P85, P103, P104, P105, P123, and mixtures thereof; Reverse Pluronic® surfactants 10R5, 17R4,17R8, 22R4,25R4, 25R5, 25R8, and mixtures thereof; Tetronic® surfactants: 304, 504, 704, 707, 904, 1104, 1304, 1504, and mixtures thereof; and Reverse Tetronic® surfactants 50R4, 50R8, 70R4, 90R8, 110R7150R8, and mixtures thereof; and mixtures thereof.

More detailed examples of the aforementioned surfactants and methods of making them are described in U.S. Pat. No. 2,674,619, Lundsted et al., issued Apr. 6, 1954; U.S. Pat. No. 3,036,118, Jackson et al., issued May 22, 1962; and U.S. Pat. No. 2,979,528, Lundsted et al., issued Apr. 11, 1961; all incorporated herein by reference in their entireties.

Polyalkyleneoxide polysiloxanes are defined by the general formula:

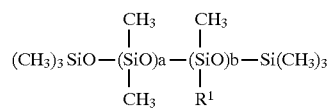

wherein a+b are from about 1 to about 50, preferably from about 3 to about 30, more preferably from about 10 to about 25, and $R^1$ is mainly one or more random or block poly(ethyleneoxide/propyleneoxide) copolymer groups having the general formula:

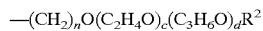

wherein n is 3 or 4, preferably 3; total c (for all polyalkyleneoxy side groups) has a value of from 1 to about 100, preferably from about 6 to about 100; d is from 0 to about 14, preferably from 0 to about 3; and more preferably d is 0; c+d has a value of from about 5 to about 150, preferably from about 9 to about 100 and each $R^2$ is the same or different and is selected from the group consisting of hydrogen, an alkyl having 1 to 4 carbon atoms, and an acetyl group, preferably hydrogen and methyl group. Examples of such compounds suitable herein include: Silwet® L-7600, L-7602, L-7604, L-7605, L-7657, and mixtures thereof; all commercially available from OSi Specialties, Endicott, N.Y.

The molecular weight of the oxyalkylene group ($R^1$) is less than or equal to 10000. Preferably, the molecular weight of the oxyalkylene group is less than or equal to about 8000, and most preferably ranges from about 300 to 5000. Thus, the values of c and d can be those numbers which provide molecular weights within these ranges. However, the number of oxyethylene units (—$C_2H_4O$) in the polyoxyalkylene groups ($R^1$) must be sufficient to render the polyalkyleneoxide polysiloxane water dispersible or water soluble. It is understood that when c is a positive number, the oxyethylene and oxypropylene units (—$C_3H_6O$) can be distributed randomly throughout the polysiloxane chain or in respective blocks of oxyethylene and oxypropylene units or a combination of random and block distributions. The preparation of polyalkyleneoxide polysiloxanes is well known in the art. Such compounds can be prepared according to the procedure set forth in U.S. Pat. No. 3,299,112, incorporated herein by reference.

The total surfactant level used in the present compositions is from about 0.05% to about 15%, more preferably from about 0.1% to about 12%, by weight of the composition. If a hydrophobic antimicrobial agent is included, more surfactant(s) should be included, typically from about 0.5% to about 10%, by weight of the composition.

AQUEOUS CARRIER: The cyclodextrins useful in the present invention should be solubilized in and dispersed in an aqueous carrier. The aqueous carrier provides a clean, convenient means for applying cyclodextrin to desired skin sites. The aqueous carrier also may impart a degree of cleaning power in and of itself via washing away skin cell debris and skin secretions which bacteria feed upon, as well as the bacteria themselves.

The term "aqueous carrier", as used herein, means water and/or any water soluble materials suitable for use as solvents. Any water may be used, such as distilled, deionized, or tap water. Water not only serves as the liquid carrier for the cyclodextrins, but it also facilitates the complexation reaction between the cyclodextrin molecules and any malodorous molecules that are on the skin site when the composition is applied. The aqueous carrier of the present invention will typically comprise from about 80% to about 98%, preferably from about 85% to about 95% of the present invention's composition.

WATER-SOLUBLE ANTIMICROBIAL: The compositions may optionally but preferably contain solubilized, mild, water-soluble, antimicrobials which are effective for inhibiting and/or regulating microbial growth in the composition and/or on skin. Contamination of the compositions of the present invention by microorganisms and subsequent microbial growth can result in unsightly or malodorous compositions. Similarly, microorganisms are typically found in cyclodextrin supplies and their growth in aqueous solutions is possible. Therefore, the inclusion of antimicrobials as preservatives aids in increasing storage stability of the composition of the present invention. When included for preservative action, the water-soluble antimicrobials are included in an effective amount to prevent spoilage or prevent growth of microorganisms inadvertently added to the composition for a specific period of time. If antimicrobial action on skin is desired, water-soluble antimicrobials must be included at a level effective to perform the preservative action discussed above, and to kill and/or prevent growth of microorganisms on the skin.

Antimicrobials useful herein include biocidal and biostatic compounds (substances that kill microorganisms and/or regulate the growth of microorganisms). Suitable water-soluble antimicrobial preservatives have a solubility of 0.3% or greater. In addition, suitable preservatives are those which can come into contact with skin without high irritation potential. Preferred antimicrobial preservatives are those that are water-soluble and are effective at low levels because the water insoluble organic preservatives can form inclusion complexes with the cyclodextrin molecules and compete with the malodorous molecules for the cyclodextrin cavities, thus rendering the cyclodextrins ineffective as odor controlling actives. Preservatives suitable for use in the present compositions are fully described in *The Theory and Practice of Industrial Pharmacy*, by Lachman, Lieberman, Kanig, 3rd. Edition, pages 466–467 and 520–522 (1986), and U.S. Pat. No. 5,534,165, to Pilosof et al., issued Jul. 9, 1996, both of which are incorporated herein by reference.

It is preferable to use a broad spectrum preservative such as one that is effective both on bacteria (both gram positive and gram negative) and fungi. A limited spectrum preservative such as one that is only effective on a single group of microorganisms, for example fungi, can be used in combination with a broad spectrum preservative or other limited spectrum preservatives with complimentary and/or supplementary activity. A mixture of broad spectrum preservatives can also be used.

Preferred water-soluble preservatives include: sodium hydroxymethylglycinate (i.e. Suttocide® A. from Sutton Labs, Chatham, N.J.), cyclic organic nitrogen compounds including imidazolidinedione compounds (such as dimethyloldimethylhydantoin i.e., Glydant® Plus from Lonza, Fair Lawn, N.J.; diazolidinyl urea and imidazolidinyl urea) and polymethoxy bicyclic oxazolidine; phenyl and phenoxy compounds including benzyl alcohol, 2-phenoxyethanol and hexamidine isethionate; quaternary ammonium compounds including polyhexamethylene biguanide; low molecular weight aldehydes including formaldehyde and glutaraldehyde; halogenated compounds including chlorhexidine, chlorobutanol, and dibromopropamidine; and mixtures thereof.

Preferred levels of antimicrobial are from about 0.0001% to about 0.6%, more preferably from about 0.0002% to about 0.55%, most preferably from about 0.0003% to about 0.5%, by weight of the composition.

HYDROPHOBIC ANTIBACTERIAL AGENTS: Optionally, the present invention may include hydrophobic antibacterial compounds to help destroy and/or control the amount of bacteria present on the skin, which aids in body odor control. However, hydrophobic antibacterial agents can form inclusion complexes with the cyclodextrin molecules and compete with the malodorous molecules for the cyclodextrin cavities, thus rendering the cyclodextrins ineffective as odor controlling actives. To account for this, the level of cyclodextrin may be adjusted as desired. Hydrophobic antibacterials useful in the present invention include triclosan, triclocarbon, eucalyptol, menthol, methylsalicylate, thymol, and mixtures thereof. Preferred are triclosan and triclocarbon. When included in the composition of the present invention, the hydrophobic antibacterials may be at a level of from about 0.1% to about 1.5% and preferably from about 0.1% to about 0.3%, by weight of the composition.

pH: Aqueous compositions of the present invention should have a pH of from about 3 to about 10, preferably from about 3.5 to about 8, more preferably from about 3.5 to about 6. Some conventional buffering agents are known in the prior art which may be used to adjust the pH to the desired level if necessary. For example, combinations of salts and acids, such as the following examples: sodium lactate, sodium citrate, potassium phosphate, lactic acid, citric acid, phosphoric acid, sodium hydroxide, and hydrochloric acid are useful. Some of the effectiveness of these ingredients may be lost as they complex with the cyclodextrin, so care is taking in formulating to adjust for that. Other optional buffers appear in *The Theory and Practice of Industrial Pharmacy*, Lachman, Lieberman and Kanig, Third Edition, incorporated herein by reference.

OPTIONAL INGREDIENTS: The present composition may also optionally comprises low molecular weight polyols. The phrase "low molecular weight polyols", as used herein, refers to linear organic compounds with more than one alcohol functional group per molecule wherein the molecular weight is less than 95. Low molecular weight polyols with relatively high boiling points, as compared to water, such as propylene glycol and glycerol are preferred ingredients which may improve odor control performance of the composition of the present invention. Cyclodextrins prepared by processes that result in a level of such polyols are highly desirable, since they can be used without removal of the polyols.

Optimally, the low molecular weight polyols will be added at a level effective to assist in complex formation without significantly reducing available cyclodextrin capacity to absorb the malodor molecules having larger sizes. Typically, low molecular weight polyols are added to the composition of the present invention at a level of from about 0.01% to about 1%, by weight of the composition, preferably from about 0.02% to about 0.5%, more preferably from about 0.03% to about 0.3%, by weight of the composition.

The composition of the present invention can also, optionally, contain adjunct odor-controlling materials, such as zinc salts, water-soluble cationic polymers, water-soluble anionic polymers, water-soluble carbonate salts, water-soluble bicarbonate salts, zeolites, and activated carbon; chelating agents; colorants; and/or antiperspirants.

Optionally, but highly preferred, the present invention can include zinc salts for added odor absorption and/or antimicrobial benefit for the cyclodextrin solution. Zinc compounds have been used to ameliorate malodor, e.g., in mouth wash products, as disclosed in U.S. Pat. No. 4,325,939, issued Apr. 20, 1982 and U.S. Pat. No. 4,469,674, issued Sep. 4, 1983, to N. B. Shah, et al., both of which are incorporated herein by reference in their entireties. Highly-ionized and water soluble zinc salts, such as zinc chloride, provide the best source of zinc ions. Zinc phenolsulfonate is preferred for use in the skin composition of the present invention; although others may also fall within the scope of the present invention. However, care must be taken in selecting zinc salts as well as their levels, since some may be irritants to the skin and therefore are not preferred for use in the present invention.

These zinc salts aid in absorbing low molecular weight amine and sulfur-containing compounds. Low molecular weight amines and/or low molecular weight sulfur-containing materials such as sulfide and mercaptans; are components of many types of malodors such as food odors (garlic, onion), breath odor, urine odors, and particularly body/perspiration odor. When zinc salts are added to the composition of the present invention they are typically present at a level of from about 0.1% to about 10%, preferably from about 0.2% to about 8%, more preferably from about 0.3% to about 5%, by weight of the composition.

Some water-soluble polymers such as water-soluble cationic polymer and water-soluble anionic polymers can be used in the composition of the present invention to provide additional odor control benefits. Water-soluble cationic polymers such as those containing amino functionalities, amido functionalities, and mixtures thereof, are useful in the present invention to control certain acid-type odors. Water-soluble anionic polymers such as polyacrylic acids and their water-soluble salts are useful in the present invention to control certain amine-type odors. Preferred polyacrylic acids and their alkali metal salts have an average molecular weight of less than about 20,000, more preferably less than 5,000. Polymers containing sulfonic acid groups, phosphoric acid groups, phosphonic acid groups, and their water-soluble salts, and mixtures thereof, and mixtures with carboxylic acid and carboxylate groups, are also suitable.

Water-soluble polymers containing both cationic and anionic functionalities are also suitable. Examples of these polymers are given in U.S. Pat. No. 4,909,986, issued Mar. 20, 1990, to N. Kobayashi and A. Kawazoe, incorporated herein by reference, in its entirety. Another example of water-soluble polymers containing both cationic and anionic functionalities is a copolymer of dimethyldiallyl ammonium chloride and acrylic acid, commercially available under the trade name Merquat 280® from Calgon. While the aforementioned water soluble polymers are useful in the present invention, when using these materials, care must be taken to insure no residual acrylic acid is present due to safety concerns associated with the presence of acrylic acid.

Water-soluble alkali metal carbonate and/or bicarbonate salts, such as sodium bicarbonate, potassium bicarbonate, potassium carbonate, sodium carbonate, and mixtures thereof can be added to the composition of the present invention in order to help to control certain acid-type odors. Preferred salts are sodium carbonate monohydrate, potassium carbonate, sodium bicarbonate, potassium bicarbonate, and mixtures thereof. When these salts are added to the composition of the present invention, they are typically present at a level of from about 0.1% to about 5%, preferably from about 0.2% to about 3%, more preferably from about 0.3% to about 2%, by weight of the composition. It is also preferred that incompatible metal salts not be present in the invention. Therefore, when these salts are used, the composition should be essentially free of zinc and other incompatible metal ions, e.g., Ca, Fe, etc. which form water-insoluble salts.

Aminocarboxylic acid chelating agents such as ethylenediaminetetraacetic acid (EDTA) can optionally be added to the composition of the present invention (preferably in the absence of any added metal ions) in order to enhance the activity of the water-soluble, antimicrobial preservative. When a chelating agent is added to the composition of the present invention, it is typically present at a level of from about 0.001% to about 0.3%, preferably from about 0.01% to about 0.2% by weight of the composition.

Zeolites can also be used in the present invention. A preferred class of zeolites are characterized as "intermediate" silicate/aluminate zeolites, particularly for use in absorbing amine-type odors. "High" zeolites are preferred for control of sulfur-containing odors, e.g., thiols, mercaptans. Zeolites, both "intermediate" and "high", are explained more fully in U.S. Pat. No. 5,429,628, to Trinh et al., issued Jul. 4, 1995, which is incorporated herein by reference in its entirety.

The carbon material suitable for use in the present invention is the material well known in commercial practice as an absorbent for organic molecules and/or for air purification purposes. Often, such carbon material is referred to as "activated" carbon or "activated" charcoal. Such carbon is available from commercial sources under such trade names as; Calgon-Type CPG®; Type PCB®; Type SGL®; Type CAL®; and Type OL®.

Colorants and dyes can be optionally added to the odor absorbing compositions for visual appeal and performance impression. When colorants are used, care must be taken in the selection of choosing dyes that will not color skin at the levels used. Preferred colorants for use in the present compositions are highly water-soluble dyes, e.g., acid blue 3, acid blue 104, acid green 1, acid green 25, acid yellow 3, acid yellow 73 sodium salt, D&C green no. 5, 6 & 8, D&C yellow no. 7, 8, 10 & 11, D&C violet no. 2, FD&C blue No. 1 & 2, FD&C green no.3, FD&C yellow no. 5 & 6, and mixtures thereof.

Optionally, the present skin composition may also comprise known antiperspirants and/or other known deodorant compositions not explicitly disclosed previously. Examples of antiperspirants appropriate for aqueous solutions include aluminum-zirconium tetrachlorohydrex glycine, aluminum-zirconium pentachlorohydrate, aluminum sesquichlorohydrate, or aluminum chlorhydrate and mixtures thereof.

PROCESS OF MAKING COMPOSITIONS

The compositions may be prepared by oil-in-water emulsion techniques such as are commonly known in the art. Examples of such techniques are described in *Remington's Pharmaceutical Science*, Eighteenth Edition, pp. 304–306, 1990, incorporated herein by reference. The compositions of the present invention also may be prepared by a process comprising the steps of: Making a first mixture by mixing surfactant(s) and an oil phase until homogenous and adding an aqueous phase with mixing until the mixture is homogenous. Making a solution by adding cyclodextrin to an aqueous phase with mixing until the cyclodextrin dissolves. Making a second mixture by mixing the solution with the first mixture until the second mixture is homogenous. Where desired, the second mixture may be diluted by adding an aqueous phase with mixing until homogenous. Where hydrophobic antimicrobials also comprise the compositions, the process of making the mixture in the first step additionally comprises adding a premix with mixing to the surfactant(s) and the oil phase until homogenous, wherein the premix is prepared by mixing a hydrophobic antimicrobial with surfactant(s) until the premix is homogenous. The term "homogenous", as used herein, means a uniformly dispersed solution. Homogeneity is indicated by a substantially smooth, lump-free and uniform appearing composition. A stable emulsion remains homogeneous over a given period which is determined by the required shelf life of the composition.

As an alternative to making the mixture by mixing surfactant(s), an oil phase, and an aqueous phase; an emulsion concentrate comprising surfactant(s), an oil phase, and a minimal amount of aqueous carrier may be used. Emulsion concentrates useful in the present invention will be from about a 3-fold to about a 20-fold concentrate. The concentrated emulsion may then be diluted by adding aqueous carrier followed by addition of the remaining ingredients as discussed above.

Other variations of processes of making the compositions of the present invention should be readily apparent to those having ordinary skill in the art. For instance, the mixture could be made in one step by addition and mixing of each of the ingredients. Alternatively, less than all of the ingredients may be pre-combined for subsequent combination with other ingredients or with other pre-combined ingredients to form the composition.

Equipment suitable for forming the mixtures and emulsion may be selected from those which are known or become known in the art. For example, suitable apparatii include dual propeller blade mixers. A turbine mixer and an in-line homogenizer using tandem rotor-stators, as described in the above-referenced U.S. Pat. No. 5,043,155, may also be used.

The resultant emulsion containing the ingredients in their total amounts has a preferred viscosity at room temperature (i.e., 20°–25° C.) in the range of from about 10 to about 200 centipoise more preferably from about 15 to about 150 centipoise; most preferably from about 20 to about 100 centipoise.

Since the compositions herein are applied directly to skin, various applicators are useful for delivering the compositions to the entire body for maximum odor control. For example, the compositions are preferably deposited on a paper product such as a wipe which later is contacted with the skin to transfer the composition to the skin.

Any wipe structures and/or methods of making the wipe structures commonly known in the art may be used. The wipe comprises a flexible dispensing means. The term "flexible dispensing means", as used herein, includes papers, cloths, non-wovens, films, foams, sponges, rollers, pads, tissues, cotton balls, and the like. Preferred wipe substrates comprise a porous material, such as the non-woven substrates, foams, or sponges, which are capable of holding the composition within the pores of the substrates. Examples of cellulosic non-wovens particularly useful and economic are described in U.S. Pat. No. 4,191,609, Trokhan, issued Mar. 4, 1980. Further description of useful wipes and methods of making said wipes are found in World Patent 95/17175, to Mitra et. al, publication date of Jun. 29, 1995. Both references are incorporated herein by reference in their entireties.

Techniques for combining the wipe substrates with the compositions herein are well known in the art. Examples of common techniques include coating, immersing, dipping, or spraying the wipe substrates with the compositions herein. The compositions herein are added to the wipe substrate at level sufficient to provide the desired odor control and/or other desired skin benefits. A convenient method of combining the composition with the chosen substrate is to place the substrate inside an open package which will ultimately house the finished product until use. The composition is poured onto the substrate and allowed to distribute throughout. It is preferred that the homogenous composition is poured onto each wipe individually rather than onto a stack of wipes. The package is then closed and the wipes ready for use.

The compositions can also be delivered as a liquids via a spray dispenser or a bottle. Preferred is a manually activated spray dispenser to avoid the use of aerosols which may be irritating to sensitive areas of the body. Spray dispensers are described more fully in U.S. Pat. No. 5,534,165 which is incorporated herein by reference in its entirety.

METHODS OF USE

The present invention encompasses methods of reducing body odor comprising the application of compositions herein onto skin. The present invention also encompasses methods of reducing vaginal odor comprising applying the compositions herein onto a pelvic region, external vagina, and/or panty-line. However, the compositions herein should not be inserted into the vagina, nor applied onto the vulva. An "effective amount" of the compositions of the present invention, as used herein, means an amount sufficient to absorb body odor so that it is less noticeable by the human sense of smell. While the determination of an effective amount used and the number of uses per day is ultimately left to the discretion of the user, typically an effective amount will be from about 0.05 to about 0.50 grams of odor absorbing composition per use, applied about 1 to about 15 times daily, for as many days as desired by user.

The compositions of the present invention are topically applied directly to the skin or hair. The compositions can be delivered by placing the composition into a dispensing means and applying an effective amount via spraying or rubbing the composition onto the desired skin surface; typically the entire body. Preferably the dispensing means is a wipe comprising a flexible dispensing means. Distribution of the composition of the present invention can also be achieved by using a hand. Alternatively, the user may combine the composition of the present invention with a flexible dispensing means of his or her own choosing. To do this, the user simply chooses a flexible dispensing means such as a washcloth; pours a solution of the composition of the present invention from a bottle or other suitable container over the flexible dispensing means, and applies the composition to the skin. In this manner, the user may use as much or as little of the composition of the present invention as he/she desires, depending upon their intended use and degree of odor control necessary.

The following non-limiting examples illustrate formulations and methods of use of the present invention.

EXAMPLES I, II, and III

|  | Example I | Example II | Example III |
|---|---|---|---|
| Pluronic ® L-44 |  | 0.15 | 0.30 |
| Pluronic ® L-43 | 0.20 |  |  |
| Silwet ®L-7657 |  |  | 0.30 |
| Silwet ® L-7605 |  | 0.15 |  |
| Silwet ®L-7600 | 0.20 |  |  |
| Dimethicone | 2.00 | 1.00 | 2.00 |
| Triclosan |  |  | 0.15 |
| Hydroxy Propyl Beta Cyclodextrin | 1.00 | 5.00 | 2.00 |
| Zinc Phenolsulfonate | 1.01 | 1.01 |  |
| Ascorbic Acid | 0.40 | 1.75 | 2.00 |
| Glydant ® Plus | 0.30 | 0.30 | 0.30 |
| Suttocide ® A |  | 0.25 |  |
| Propylene Glycol | 1.00 | 1.00 | 1.00 |
| Water | Balance | Balance | Balance |

Alternatively, the hydroxy propyl beta cyclodextrin in the above examples could be substituted with other beta cyclodextrins, alpha-cyclodextrins, gamma-cyclodextrins, or mixtures of these cyclodextrins and/or their derivatives. Similarly, the examples could comprise other hydrophobic antimicrobials.

Prepare Examples I–III as follows: Prepare a premix by mixing triclosan with about ⅙, by weight, of total Pluronic® L and Silwet® L (Example III only). Prepare a first mixture by mixing about 1% of water, by total formula weight, with surfactant. For Example III, preparing the first mixture also includes a final step of adding the premix with mixing. Using a sonifier, prepare a second mixture by adding dimethicone to the first mixture, then slowly adding about 1%–2% of water, by total formula weight. Prepare premix (a) by mixing hydroxypropyl beta cyclodextrin and about 1.5%–3% of water, by total formula weight; premix (b) by mixing zinc phenolsulfonate and about 2% of water, by total formula weight; premix (c) by mixing the ascorbic acid and about 2% of water by total formula weight; and premix (d) by mixing Glydant® Plus and propylene glycol. Using a homogenizer, add remaining water to the second mixture to create a third mixture. Add premixes (a), (b), (c), and (d) to the third mixture using the homogenizer.

Preparation for Application to Skin: The solutions of the present invention may be loaded onto a wipe or poured into a spray device or poured directly onto the skin or flexible dispensing means of the user's choosing for convenient application to the skin. To prepare wipes, place dry fabric or wipe substance inside an open package which will ultimately contain the finished product. Pour the composition onto the fabric to distribute throughout. Close the package for storage until consumer use. To prepare spray, pour the composition into the selected spray package. Close the package for storage until consumer use.

EXAMPLE IV

A woman with stress urinary incontinence finds that the wetness associated with this condition causes vaginal odor which she wants to remove from the skin and control. After urinating, the woman wipes her external vagina with a wipe containing the composition in Example I. The cyclodextrin and zinc salts in the composition complex with body odors such as polycyclic compounds and amines (respectively) which are found in urine. This woman notices less body odor after using the wipes.

EXAMPLE V

A large-breasted woman finds that when she exercises, she tends to experience sweating and skin chafing under the breasts. Before and after exercising, she applies the composition from Example II via a hand-held trigger-spray bottle. She sprays the composition under her breasts and notices less body odor and feels more comfortable after using the spray.

EXAMPLE VI

A man has severe allergies to cosmetic deodorants, antiperspirants, heavy cologne, and avoids using such products. This results in uncontrolled and embarrassing body odor. His doctor suggests applying the mild odor absorbing composition of Example III after showering. The man applies the composition to his entire body via a spray after showering each morning, and suffers no allergic reaction. The man feels comfortable without the embarrassment of uncontrollable body odor. The man carries a pouch of wipes which also contain the composition of Example III for convenient and discrete reapplication as needed.

What is claimed:

1. A method of reducing body odor comprising the application to skin of an odor absorbing composition comprising:

a. from about 0.1% to about 5%, by weight of the composition, of solubilized, water-soluble, uncomplexed cyclodextrin;

b. from about 0.1% to about 36%, by weight of the composition, of an oil phase selected from the group consisting of emollients, moisturizers, and skin protectants;

c. one or more surfactants each having a hydrophilic/lipophilic balance of about 8–18 and wherein each surfactant, when combined with an aqueous cyclodextrin solution, provides no less than about 25% a level of odor capture as an aqueous cyclodextrin solution; and d an aqueous carrier;

wherein the composition is safe for use on the skin.

2. The method according to claim 1 wherein the surfactant is selected from the group consisting of block copolymers of polyoxyethylene-polyoxypropylene, polyalkyleneoxide polysiloxanes, and mixtures thereof.

3. The method according to claim 2 wherein each surfactant, when combined with an aqueous cyclodextrin solution, provides no less than about 75% of odor capture as an aqueous cyclodextrin solution.

4. The method according to claim 1 wherein the composition further comprises one or more antimicrobials selected from the group consisting of hydrophobic antimicrobials, water soluble antimicrobials, and mixtures thereof.

5. The method according to claim 1 wherein the composition further comprises one or more adjunct odor controlling materials selected from the group consisting of zinc salts, zeolites, activated carbon, water-soluble carbonates, water-soluble bicarbonates, and mixtures thereof.

6. The method according to claim 1 wherein the cyclodextrin is selected from the group consisting of beta-cyclodextrins, derivatives of beta-cyclodextrins, alpha-cyclodextrins, derivatives of alpha-cyclodextrins, gamma-cyclodextrins, derivatives of gamma-cyclodextrins, and mixtures thereof.

7. The method according to claim 1 wherein the cyclodextrin is selected from the group consisting of methylated cyclodextrin, hydroxypropyl beta-cyclodextrin, and mixtures thereof.

8. A method according to claim 4 wherein the hydrophobic antimicrobial is selected from the group consisting of triclosan, triclocarbon, eucalyptol, methylsalicylate, and thymol; and is present at a level of from about 0.1% to about 1.5% by weight of the composition.

9. The method according to claim 1 wherein the application is accomplished using a flexible dispensing means.

10. A method of reducing vaginal odor comprising the application to a pel vic region, an external vagina, and/or a panty line of an odor absorbing composition comprising:
  a. from about 0.1% tho about 5%, by weight of the composition, of solubilized, water-soluble, uncomplexed cyclodextrin;
  b. from about 0.1% to about 36%, by weight of the composition, of an oil phase selected from the group consisting of emollients, moisturizers, and skin protectants;
  c. one or more surfactants each having a hydrophilic/lipophilic balance of about 8–18 and wherein each surfactant, when combined with an aqueous cyclodextrin solution, provides no less than about 25% a level of odor capture as an aqueous cyclodextrin solution; and
  d. an aqueous carrier;
wherein the composition is safe for use on skin.

11. The method according to claim 10 wherein the surfactant is selected from the group consisting of block copolymers of polyoxyethylene-polyoxypropylene, polyalkyleneoxide polysiloxanes, and mixtures thereof.

12. The method according to claim 11 wherein each surfactant, when combined with an aqueous cyclodextrin solution, provides no less than about 75% of odor capture as an aqueous cyclodextrin solution.

13. The method according to claim 10 wherein the composition further comprises one or more antimicrobials selected from the group consisting of hydrophobic antimicrobials, water soluble antimicrobials, and mixtures thereof.

14. The method according to claim 10 wherein the composition further comprises one or more adjunct odor controlling materials selected from the group consisting of zinc salts, zeolites, activated carbon, water-soluble carbonates, water-soluble bicarbonates, and mixtures thereof.

15. The method according to claim 10 wherein the cyclodextrin is selected from the group consisting of beta-cyclodextrins, derivatives of beta-cyclodextrins, alpha-cyclodextrins, derivatives of alpha-cyclodextrins, gamma-cyclodextrins, derivatives of gamma-cyclodextrins, and mixtures thereof.

16. The method according to claim 10 wherein the cyclodextrin is selected from the group consisting of methylated cyclodextrin, hydroxypropyl beta-cyclodextrin, and mixtures thereof.

17. The method according to claim 13 wherein the hydrophobic antimicrobial is selected from the group consisting of triclosan, triclocarbon, eucalyptol, methylsalicylate, and thymol; and is present at a level of from about 0.1% to about 1.5% by weight of the composition.

18. The method according to claim 10 wherein the application is accomplished using a flexible dispensing means.

19. The method according to claim 4 wherein the water soluble antimicrobial is sodium hydroxymethylglycinate.

20. A method of reducing vaginal odor comprising the application to a pelvic region, an external vagina, and/or a panty line of an odor absorbing composition comprising:
  a. from about 0.1% to about 5%, by weight of the composition, of solubilized, water-soluble, uncomplexed cyclodextrin;
  b. from about 0.1% to about 36%, by weight of the composition, of an oil phase selected from the group consisting of emollients, moisturizers, and skin protectants;
  c. one or more surfactants each having a hydrophilic/lipophilic balance of about 8–18 and wherein each surfactant, when combined with an aqueous cyclodextrin solution, provides no less than about 25% a level of odor capture as an aqueous cyclodextrin solution;
  d. an effective amount of sodium hydroxymethylglycinate; and
  e. an aqueous carrier;
wherein the composition is safe for use on skin.

* * * * *